United States Patent
Yin et al.

(10) Patent No.: US 6,773,928 B1
(45) Date of Patent: Aug. 10, 2004

(54) COMPOSITIONS AND METHODS FOR ENHANCING BIOASSAY PERFORMANCE

(75) Inventors: Ray Yin, Newark, DE (US); H. Dupont Durst, Bel Air, MD (US); Peter A. Emanuel, Abingdon, MD (US); Gary L. Hagnauer, Wayland, MA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 277 days.

(21) Appl. No.: 09/939,884

(22) Filed: Aug. 27, 2001

Related U.S. Application Data

(63) Continuation-in-part of application No. 09/448,403, filed on Nov. 22, 1999, now abandoned.
(60) Provisional application No. 60/156,293, filed on Sep. 22, 1999.

(51) Int. Cl.$^7$ .............................................. G01N 33/543
(52) U.S. Cl. ...................... 436/518; 436/525; 436/526; 436/536; 436/539; 436/544; 436/545; 436/546; 436/823; 424/1.49; 424/1.53; 424/1.33; 424/486; 435/7.1; 528/332; 528/310; 528/363; 525/951; 564/153; 564/155; 564/486; 564/509
(58) Field of Search ................................ 436/518, 525, 436/526, 536, 539, 544, 545, 546, 823; 424/1.49, 1.53, 1.33, 486; 435/7.1; 528/332, 310, 363; 525/451; 564/153, 155, 486, 509

(56) References Cited

U.S. PATENT DOCUMENTS

| | | | |
|---|---|---|---|
| 5,338,532 A | * | 8/1994 | Tomalia et al. |
| 5,656,503 A | * | 8/1997 | May et al. |
| 5,731,095 A | * | 3/1998 | Milco et al. ................ 428/482 |
| 5,851,777 A | * | 12/1998 | Hunter et al. |
| 6,020,457 A | * | 2/2000 | Klimash et al. |
| 6,060,327 A | * | 5/2000 | Keen |
| 6,121,056 A | * | 9/2000 | Moll, III et al. |

* cited by examiner

*Primary Examiner*—Christopher L. Chin
*Assistant Examiner*—Pensee Do
(74) *Attorney, Agent, or Firm*—Ulysses John Biffoni

(57) ABSTRACT

Compositions of matter and methods for enhancing bioassay performance are disclosed. More particularly, the composition of matter comprises a molecularly compact polymer-ligand conjugate capable of self-orienting on a surface to improve the orientation of the ligand/receptor binding domains within the bioassay at the nanoscopic level. In a preferred embodiment, the molecularly compact polymer comprises a dendrimer polymer such as a fifth generation polyamidoamine dendrimer having exterior surface hydroxyl and amine functional groups, and the ligand/receptor comprises an antibody or Fab.

50 Claims, 12 Drawing Sheets

COMPOSITIONS AND METHODS FOR ENHANCING BIOASSAY PERFORMANCE

This application is a continuation-in-part of application Ser. No. 09/448,403, filed Nov. 22, 1999, now abandoned, which in turn was a non-provisional continuation of provisional application Ser. No. 60/156,293, filed on Sep. 22, 1999.

GOVERNMENT INTEREST

The invention described herein may be manufactured, used, and/or licensed by or for the United States Government.

FIELD OF THE INVENTION

This invention relates generally to nanomanipulation and, more particularly, to nano-orientation of antibody-dendrimer conjugates. The compositions of matter and methods of the present invention allow one to construct more sensitive bioassays by improving the orientation of the antibody binding domains within the bioassay at the nanoscopic level.

BACKGROUND OF THE INVENTION

This invention deals with nanomanipulation and, more particularly, nano-orientation of antibody-dendrimer conjugates to construct more sensitive and accurate immunoassays. These improved bioassays are more reproducible with virtually no false positive or false negative responses. In addition, this invention also reduces the amount of reagent used in the immunoassays, thus reducing the production and operating costs. Finally, the present invention provides the capability of using nanomanipulation to construct miniaturized nanodevices for chemical/biological (chem/bio) sensor applications.

Due to rapidly growing demands in market sectors such as medical diagnostics, high-throughput drug/gene screenings, environmental monitoring, chemical and biological defense, and domestic preparedness programs (chemical-biological antiterrorism); the development of miniaturized chem/biosensors has recently become an important R&D focus in industrial, government, and academic laboratories. Currently, most of the hospital medical diagnostic assays, combinatorial drug/gene screenings, and environmental monitoring methods are primarily based on bulky instruments such as flow cytometry, Threshold, and Origin devices. These instruments, although very sensitive, are often not suitable for environmental monitoring or domestic counter-terrorist programs due primarily to the difficult field operating conditions. Nor are they useful for home medical diagnostics because of the restrictive nature of home testing conditions. For example, dirty environmental samples often complicate the assay results, and limited power supplies in the field generate additional logistic problems. The requirement of well-trained personnel to carry out the assays also poses many practical problems for using these instruments both at home and in the field. Conversely, the high-throughput drug and gene screening industry prefers fast, sensitive, low cost, and more importantly, miniaturized sensors that only require a very small amount of sample, and are capable of detecting extremely low levels of active components.

Recently, a number of research groups have attempted to use microelectrical mechanical systems (MEMS) technology to "shrink" the existing detectors or analytical instruments through a "lab on a chip" approach. This approach utilizes microlithograghy techniques (borrowed from the microelectronic industry) to produce micron sized microfluidic cells that can perform both separation and detection at the same time. As a result, the size of the current instrument hardware could be miniaturized very dramatically, and the cost could also be significantly reduced. However, these instruments are still in development and commercial devices are not available. Moreover, this "top-down" approach only addresses problems down to about the one-micron level. Since most of the biological sensing events occur at nanoscopic level (1000 times smaller), the performance of these assays will at most remain the same as their bulky instrument counterparts. Therefore, the manipulation of these binding events at nanoscopic size scale is not only more important, but also more challenging for the further advancement of this miniaturization. In this patent we will disclose a novel nanomanipulation approach to constructing miniaturized nano-biodetectors with superior assay performance.

International patent application WO 95/24221 PCT/US95/03045 and U.S. Pat. No. 5,714,166 entitled "Bioactive and/or targeted Dendrimer Conjugates" disclose dendrimer related conjugates, however, neither of them deals with nanomanipulation and nano-orientation. Furthermore, the chemical structure of the dendrimers disclosed in these references is unlike that of the present invention. International patent application WO 95/28641 PCT/US95/04313 "Rapid Detection of Analytes with Receptors Immobilized on Soluble Submicron Particles," and WO 95/27902 PCT/US95/04547 "Random Detection of Antigens with Antibodies Immobilized on Soluble Submicron Particles," and PCT/US/96/13057 WO 97/07398 "Polypeptide-Dendrimer Complexes" also disclose using dendrimer-antibody conjugates for immunoassays. However, all of these assays are bulky instrument-based assays. Moreover, none of the above disclose the dendrimer structure of the present invention in that the present invention utilizes specific exterior surface functional groups in the dendrimer in order to tailor the dendrimer-ligand a conjugate so that it is self-orienting on a surface. For example, exterior surface functional groups including both amine and hydroxyl groups have been found particularly effective for the nanomanipulation concept, especially in a miniaturized hand-held, visual detection format.

SUMMARY OF THE INVENTION

Accordingly, it is a primary object of the present invention to provide compositions of matter and methods using nanomanipulation to improve the performance of bioassays.

It is a further object of the present invention to provide methods of using nanomanipulation to construct miniaturized biodetectors or nanodevices.

It is another object of the present invention to use these nanomanipulation methods to enhance bioassay performance, as well as reducing reagent cost and false positive responses.

The foregoing and other objects and advantages of the present invention will hereafter become more fully apparent from the following detailed description. In the description, reference will be made to examples and drawings which form a part hereof, and in which is shown by way of illustration, and not limitation, certain preferred embodiments. Such description does not represent the full extent of the invention, but rather, the invention may be employed according to the full scope and spirit of the invention as defined in the appended claims.

DETAILED DESCRIPTION OF THE INVENTION

Figure 1:
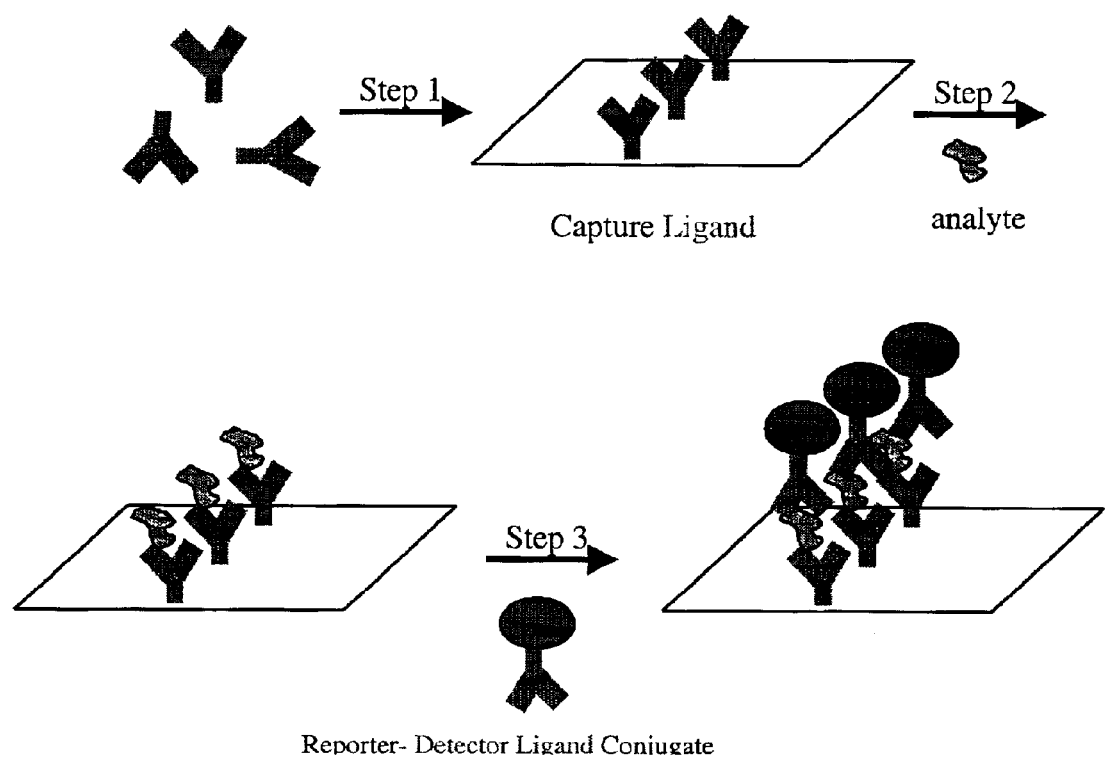
FIG. 1 is an illustration of a typical ligand-based "sandwich" assay that consists of a capture ligand, an analyte, and a detector-ligand conjugate.

Referring now to FIG. 1, a ligand based "sandwich" assay consists of three components: a capture ligand, an analyte, and a reporter (i.e. an enzyme, a fluorophore, or a colored, dyed or stained particle) that has been previously immobilized with a detector ligand. Such an assay often requires three separate experimental steps. The first step involves immobilization of capture ligands on a membrane or ELISA plate surface, followed by a subsequent addition of an analyte solution to form a ligand-analyte complex. The last step is to add a reporter group (previously immobilized with a detector ligand) to generate a capture ligand-analyte-detector ligand complex. As a result of this "sandwich" assay, the unknown analyte can be identified, and its concentration can be quantified as well. If the analyte is not present in the sample solution, no "sandwich" complex will be formed, thus no signal response will be observed.

Figure 2:
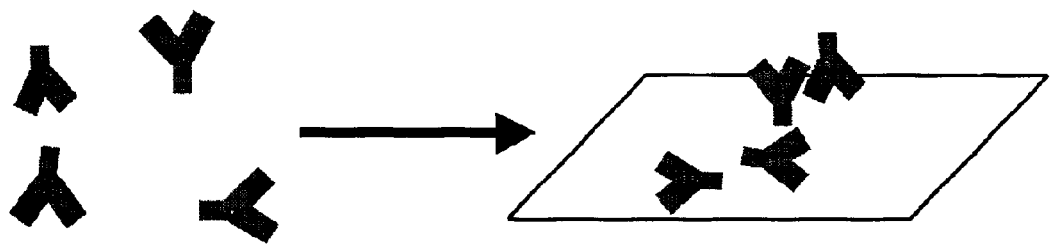
FIG. 2 is an illustration of the randomly oriented ligand immobilized through a deposition process of the prior art.

However, when directly deposited on a membrane surface or attached onto a reporter group, both capture and detector ligands are randomly oriented at the surface, see FIG. 2. In addition, due to the lack of spacer layers between these ligands and surfaces, the subsequent binding events with targeted analytes are significantly hindered due to steric effects. In some cases, due the collapse of three-dimensional structures (binding domains) of these ligands (i.e. antibodies), the recognition capability was virtually lost. The resulting assay is, therefore, much less sensitive than theoretically predicted.

The current solutions for controlling these nano-orientation and binding events (i.e. immobilizing binding ligands such as peptides, DNAs, and antibodies on a microchip surface) involve both physical deposition and chemical attachment approaches. The physical deposition strategy, although low cost, gives a completely random orientation of the binding ligands. On the other hand, the multistep chemical attachment approach provides improved orientation, however it is often too expensive, and also tends to give irreproducible results due to incomplete chemical reactions.

Figure 3:
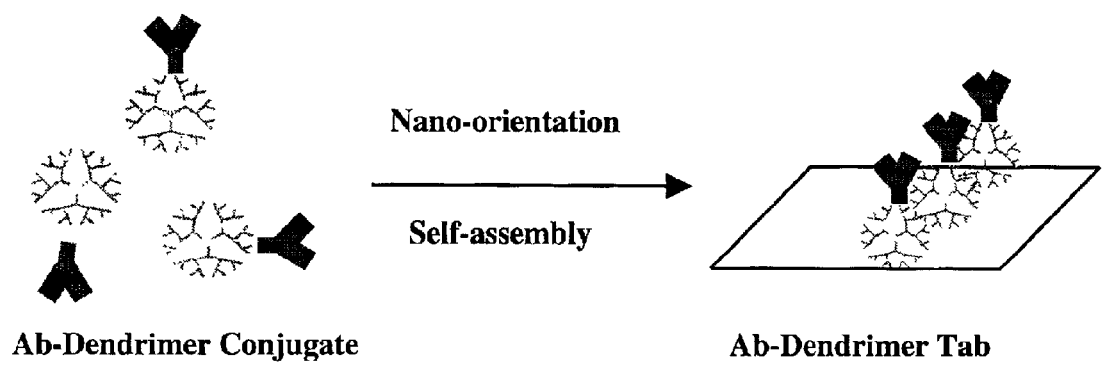
FIG. 3 is an illustration of the nanoscopically self-oriented dendrimer-ligand conjugates of the present invention at a surface such as an immunoassay ticket membrane or a colloidal particle surface.
Figure 11:
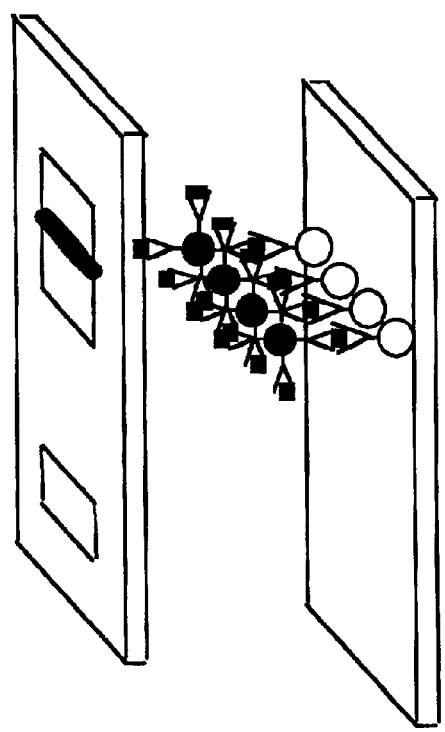
FIG. 11 is an illustration showing how the antibody binding domains (Fabs) can be oriented at a nanoscopic level through a simple self-assembly process using molecularly compact dendrimers (1–50 nm in diameter). As a result of this nanomanipulation, the performance of the nanodevice has been significantly improved.
Figure 11:
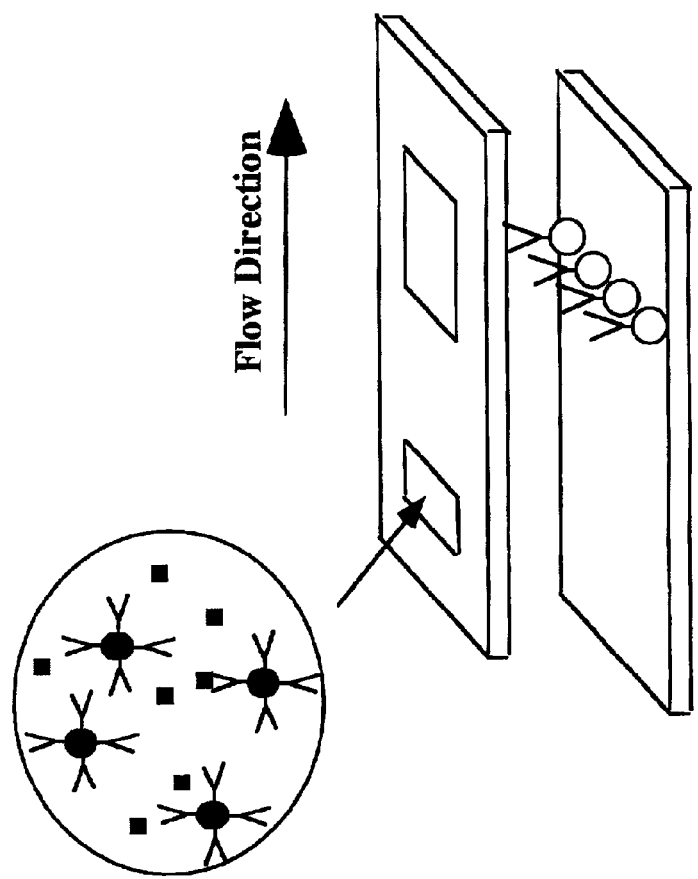
Figure 12:
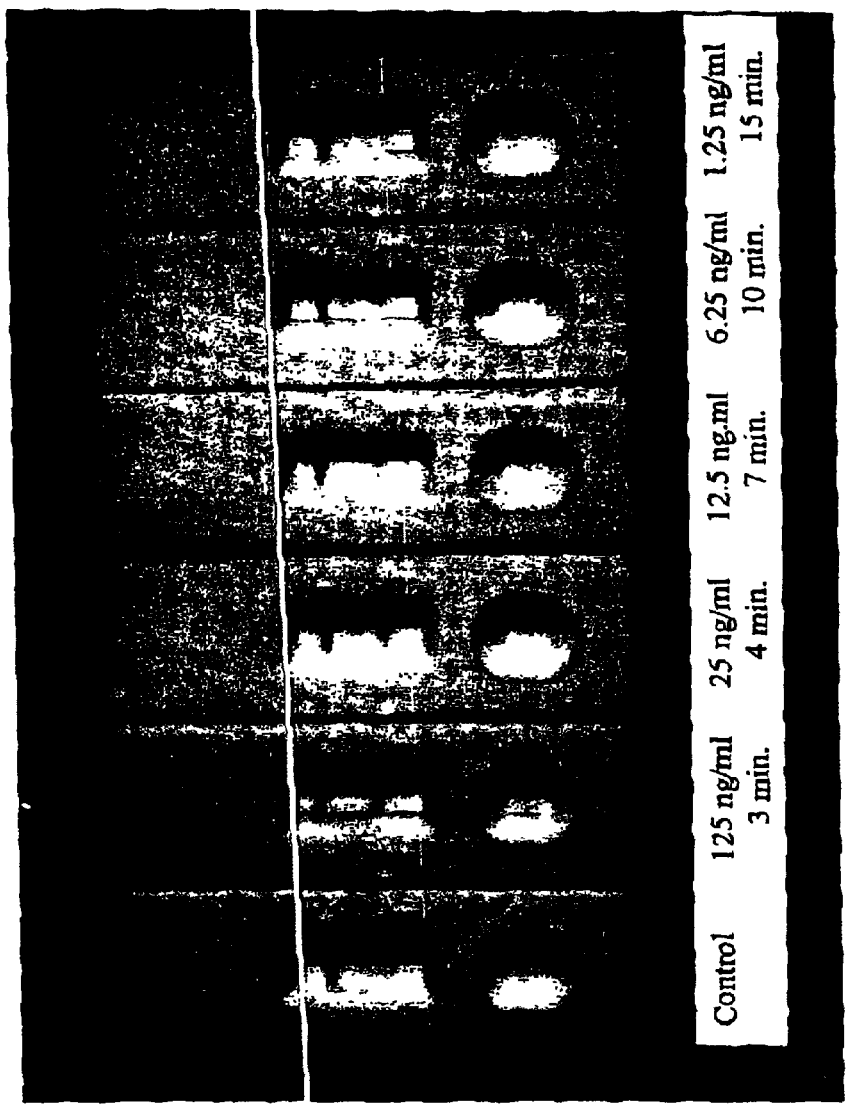
FIG. 12 is an image of developed dendrimer-based immunoassay tickets at various antigen concentrations.

To address these assay performance problems, we have recently developed a unique nanomanipulation concept that utilizes a low cost, physical deposition process that produces a highly oriented nanofilm, in which the binding ligands are perfectly aligned on the surface. The materials capable of self-orienting these binding ligands are three dimensional, tree-like polymers called dendrimers. Because of the availability of a large number of surface groups at the dendrimer's exterior, the binding ligands can be readily linked onto a dendrimer, thus generating a dendrimer-ligand conjugate. This conjugate can then be immobilized onto a membrane, a microchip, or a nanoparticle surface through a self-assembly process that is very similar to the formation of Langmuir-Blodgett (LB) films, wherein the dendrimer portion is in contact with the surface and the ligand (antibody) portion is on top of the dendrimer. This effect is even more pronounced when the dendrimer and the surface carry opposite charges and results in a self-orienting effect in which the dendrimer orients itself so that the ligand (antibody or Fab) is positioned away from the surface, see FIG. 3. As a result, the ligands or binding receptors are always oriented such that their binding domains are on the top of the nanofilm (towards the analyte), thus giving the most effective biosensing result as depicted in FIGS. 3 and 11. In addition to dendrimers, other dendritic polymers such as dendritic grafted polymers (dendrigrafts) could also be utilized for nanomanipulations.

In general, the ligand molecules include antigens (i.e. bacteria, viruses, toxins), antibodies (i.e. IgG and IgE molecules), antibody fragments, Fabs, polypeptides, hormones (i.e. insulin, hCG), neurotransmitters (i.e. acetylcholine), DNA fragments, RNA fragments, enzymes (i.e. OPAA and OPH enzymes), small molecules such as sialic acid, porphyrins, and nucleotides, or other receptor molecules well know to those of ordinary skill of art. The most preferred ligands in this invention are IgG or Fab molecules for the present applications.

Receptors are biomolecules (i.e. proteins or polysaccharides) often present on cell surface or in cell plasma. The receptors are capable of recognizing viruses, antigens, neurotransmitters, and hormones. For example, T helper cell CD4 molecule is a virus specific receptor of HIV, while T cell receptor for antigens recognizes specific antigens. Acetylcholine receptor (AChR) binds neurotransmitter acetylcholine molecule, whereas hormone receptor such as Adrenergic or insulin receptor recognizes adrenaline or insulin. Others may include Fc receptor on macrophage, which is a receptor of immunoglobulin. These receptors or receptor moieties can be isolated from the biological systems, or synthesized through either biotic or abiotic routes. Therefore, these newly developed receptor molecules or moieties can also be utilized as ligands for nanomipulation applications.

The surfaces to which the dendrimer-ligand conjugate may be bound are varied and include glass, nitrocellulose, paper, quartz, plastics, metals, colloidal particles including colloidal gold, colloidal silver and colloidal platinum, polymer latex beads, clays, ceramics, quantum dots, up-converting phosphorescent particles, and, of course, immunoassay ticket membranes. Quantum dots are inorganic nanoparticles (often less than 5 nm in diameter) capable of emitting different colors of lights by just changing their sizes. Such optical properties are well known to those of ordinary skill in the art. Up-converting phosphors are submicron ceramic microparticles that emit visible light upon excitation with near-infrared light. Such particles have sizes ranging from 100 nm to 500 nm and comprise rare earth ions, e.g., ytterbium, which are capable of absorbing two photons of infrared light. Due to the absence of autofluorescence in background, these microparticles are often utilized as a tagging moiety for biological assays.

Figure 4:
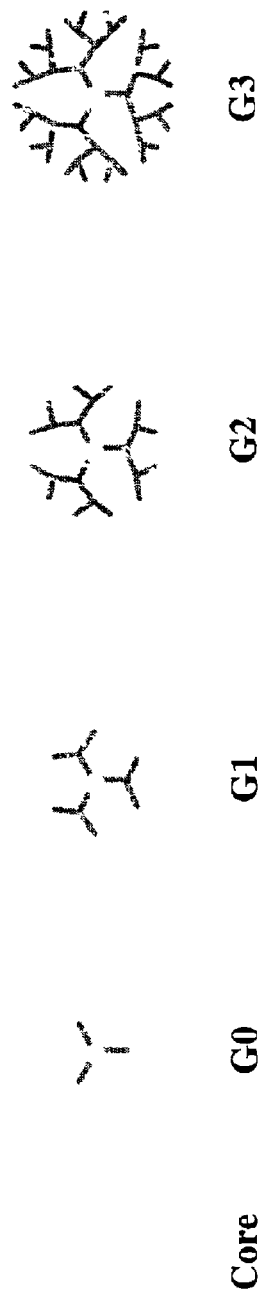
FIG. 4 is a schematic drawing of typical dendrimer and dendrigraft branching pattern.
Figure 4:
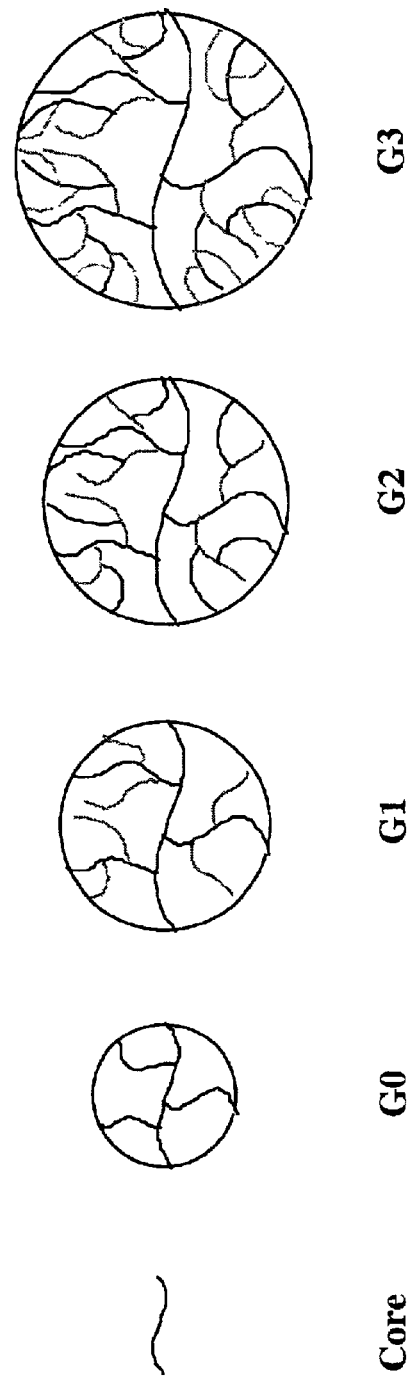

In order to further elucidate the structure-property relationship, well-defined dendrimers and dendrigrafts were selected for different assay studies. The Polyamidoamine (PAMAM) dendrimers were prepared through a repetitive synthesis method using both Michael addition and amidation reactions (Tomalia, et. al, *Polymer J.* (Tokyo) 1985, 17, 117), incorporated by reference herein. The polyethyleneneimine (PEI) dendrigrafts were obtained through a "graft upon graft" approach (Yin, et. al, *PMSE* 1995, 73, 277.), also incorporated by reference herein. Although both can be produced in a well-defined fashion, their branching patterns are very different. The dendrimer branches at its termini, while the dendrigraft grafts along its polymeric backbone. The more detailed schematic drawings for dendrimers and dendrigrafts are shown in FIG. 4. After appropriate chemical modifications, dendrigrafts with exactly the same molecular weight and surface functional groups (i.e. primary amines) as the corresponding dendrimers can be generated, thus their properties can be directly compared.

Figure 5:
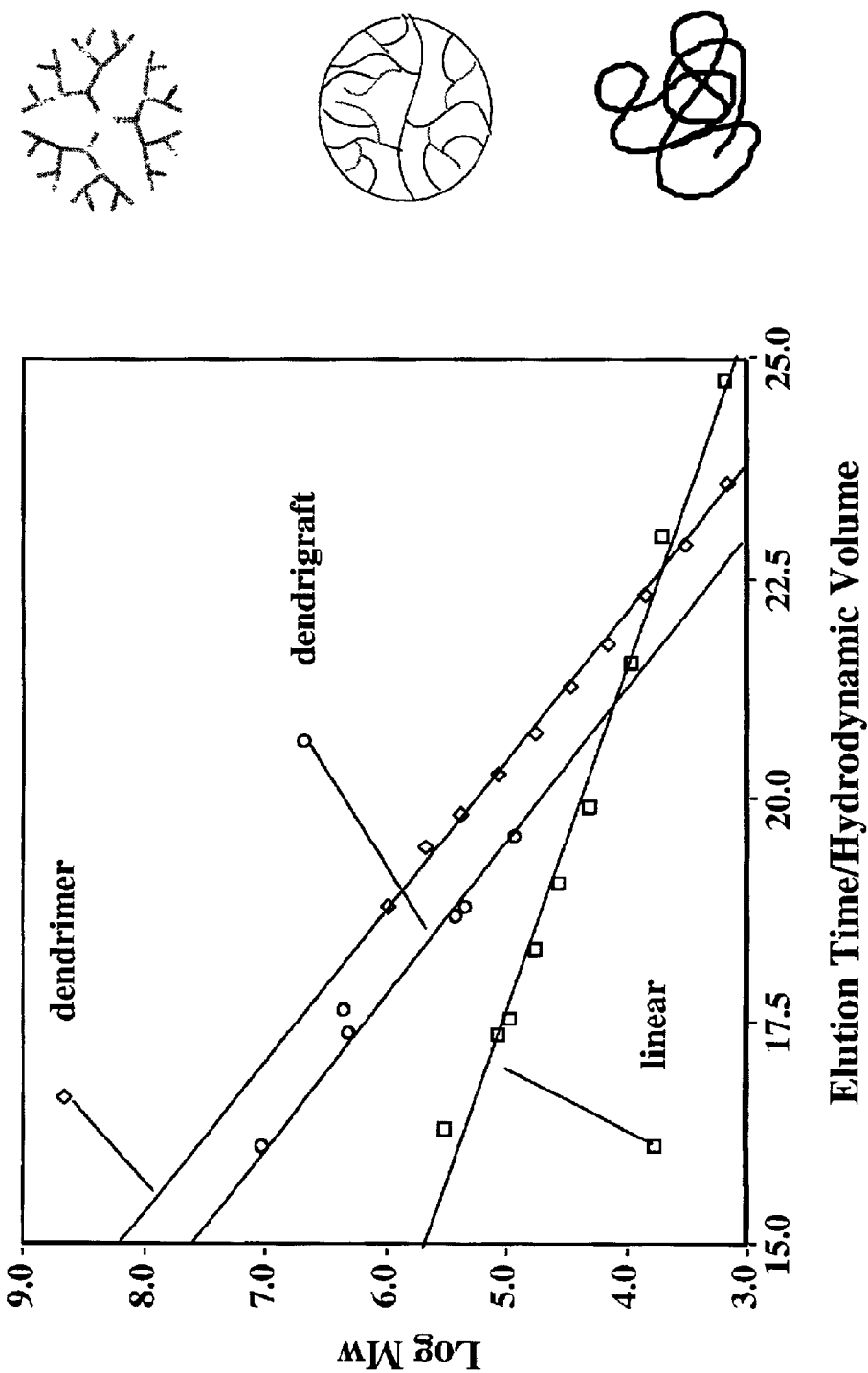
FIG. 5 is a graph showing characterization of linear and dendritic polymers by SEC-MALLS.

Since a dendrimer often possesses higher branching density than that of a dendrigraft, the former is in general more structurally compact than the corresponding dendrigraft. In contrast, due to the absence of interior branching, the linear polymers are often much more flexible than both dendrimers and dendrigrafts. Such an effect can be conveniently studied by Size Exclusion Chromatography (SEC) coupled with a Multi Angle Laser Light Scattering (MALLS) detector, wherein the SEC elution time, which in turn reflects the hydrodynamic volume of a polymer, can be directly correlated to the absolute molecular weight (MW) obtained from an on-line MALLS detector. From FIG. 5, it can be seen that at the same elution volume (<21 min) or hydrodynamic volume, the dendrimer has the highest MW, followed by the dendrigraft, while the linear polymer possesses the lowest MW. This indicated that the dendrimer exhibits the most compact molecular structure, followed by the dendrigraft, and finally the linear polymer.

Since the compact molecular structure is one of the key parameters for nanomanipulation designs, three candidate polymers (i.e. linear polymers, dendrigrafts, and dendrimers) with exactly the same molecular weight were chosen for assay performance studies. When the same ligand (i.e. an antibody) is attached onto these different 3-dimensional (3-D) polymers through reductive, oxidative, or heterolinker couplings (see experimental section), the resulting assay performance can be directly compared. Due to the lack of exterior surface functional groups, the linear synthetic polymers such as polyethylene glycol or oxide do not give good nano-orientation results. The linear protein molecules such as protein A or other secondary antibodies, if folded, improve nano-orientation to some extent. However, they tend to be denatured very rapidly especially under extreme pHs and temperatures, thus generating inconsistent assay results.

Figure 6:
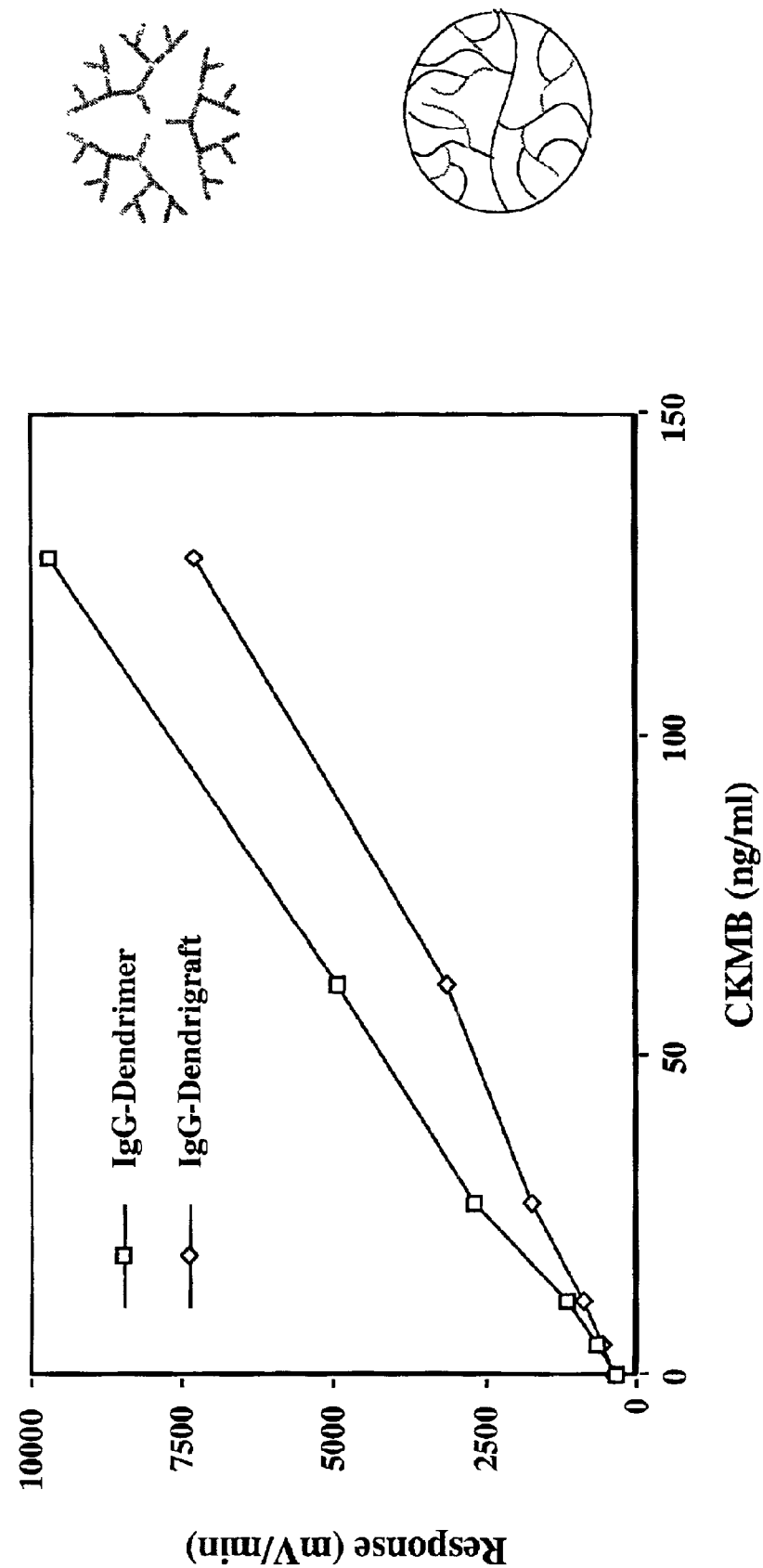
FIG. 6 is a graph showing a comparison of performance between IgG-dendrimer and IgG-dendrigraft conjugates in solid-phase immunoassays.

Therefore, our demonstration has mainly focused on comparing two close relatives, namely dendrimers and dendrigrafts, for nanomanipulation studies. In this case, dendrimers and dendrigafts with exactly the same MW (30K, measured by MALLS) and functionality (primary amine surface group) were utilized for bioconjugation reactions, and the subsequent CKMB (creatine kinase muscle bone) solid-phase immunoassays. From FIG. 6, it can be seen that the dendrimer-based assay gave better sensitivity than that of the dendrigrafts (by about 25%). This result indicated that the molecularly compact structure of these 3-D polymers did play an important role in this nanomanipulation process, and, therefore, affected the assay performance very significantly. The compactness of the dendritic polymers is dependent upon and varies from generation to generation, and an ideal dendritic polymer has 100% branching, i.e., no defects or linear branching throughout the structure.

In general, the preferred polyamidoamine dendrimer generations are from G1 to G10. The more preferred are from G3 to G8, and the most preferred generation is G5 for polyamidoamine dendrimers. For polyethyleneimine dendrigrafts, the preferred generations are from G1 to G5, the more preferred are from G2 to G4, and the most preferred is G3. The preferred size varies and the selection of most preferred sizes also depends on the size of the receptors. For example, for IgG and Fab molecule based receptors or ligands, the preferred polyamidoamine dendrimer generations are from G2 to G8 having sizes of 2.9 to 9.7 nm in diameter, respectively. The more preferred are from G4 to G6 having sizes of 4.5 to 6.7 nm in diameter, respectively, and the most preferred is G5 having a diameter of 5.4 nm. The dendrimer size is critical because if the dendrimer is too small, for example, less than 2.0 nm, and the ligand size is too large, for example, greater than 10.0 nm, the polymer-ligand conjugate will be incompatible for proper surface orientation. Size compatibility between the dendrimer and ligand in the dendrimer-ligand conjugate is critical for proper orientation on surfaces, which in turn is critical for ensuring and improving the accuracy of bioassays. Of course, the size of the dendrimer is determined by the generation, and the size of the ligand or receptor can be matched with an appropriately sized dendrimer to ensure proper orientation of the ligand when the dendrimer is bound to a surface. Once the size is determined, the nanoorientation effect seems to be independent of specific chemical structures at the dendrimer interior. In this case, both polyamidoamine (PAMAM dendrimer manufactured by Dendritech) and polypropylene amine (PA dendrimer manufactured by DSM) dendrimers with similar sizes (i.e. around 5 nm in diameter) and surface groups gave the same nanoorientation effect and assay performance.

In addition to compactness or size, the functionality of these dendritic polymers also affects the assay performance very significantly. The selection of functional groups is based on three criteria: 1) ease of conjugation; 2) surface adhesion strength; and 3) the amount of non-specific binding between capture and reporter groups. A facile conjugation strategy could significantly reduce the cost of the reagent, as well as increase the lot-to-lot reproducibility. The enhancement of surface adhesion between the dendritic polymers and a surface automatically triggers the self-assembly process on the surface (i.e. a membrane, a chip, or a particle), thus giving the best nano-orientation results. Non-specific bindings between capture (i.e., dendrimer-ligand conjugate) and reporter (i.e., dendrimer-ligand-reporter conjugate) groups often results in false positive readings, and, therefore, need to be minimized. For the CKMB assays, since the reporter system is enzyme-based and the substrate is a small molecule, the non-specific binding problem is not very pronounced. However, for visual assays that rely on colored colloidal metal particles (i.e. gold or silver) or dye encapsulated/labeled polymer beads, the non-specific bindings between dendrimers (in capture portion) and colloidal particles or beads (in reporter portion) are often very pronounced, thus resulting in very significant false positive problems.

Therefore, the density of dendrimer surface groups (i.e. primary amines) needs to be reduced in order to minimize these interactions. This can often be achieved by choosing smaller sized dendrimers, where a smaller number of primary amine groups are present. Alternatively, the relative number of primary amine groups at the dendrimer surface can be reduced by introducing non-ionic or anionic functionalities such as those selected from the group consisting of hydroxyls, amides, esters, ketones, aldehydes, carboxylic acids and salts, ethers, aliphatic or aromatic groups, nitrites, and nitrocompounds. The exterior surface groups of the dendrimer will then comprise the amines in combination with one or more of the aforementioned functional groups. More preferred are non-ionic functional groups containing hydroxyls and amides (i.e. acetamido group), with the hydroxyl group being most preferred.

However, the dendrimer can not be too small, since a conjugate consisting of a smaller dendrimer and a larger ligand or receptor may very well lose its desired orientation. Moreover, the percentage of non-ionic groups on a PAMAM dendrimer surface can not be too high, otherwise a strong adhesion between the dendrimers and the surface can not be maintained. In general, a combination of these parameters are often considered in order to construct the best assay system. For example, the percentage of hydroxyl groups in a G5 (generation 5, MW=30,000) PAMAM dendrimer having mixed OH and $NH_2$ exterior surface functional groups can range from 1 to 99% OH. For the present invention, the preferred percentage of hydroxyl groups is from 20 to 90%, the more preferred percentage is from 50 to 85%, and the most preferred is about 75% OH and 25% $NH_2$ on an G5 PAMAM dendrimer.

Therefore, both dendrimer and ligand size compatibility, and the optimization of surface functional groups on the dendrimer can be used to produce dendrimer-ligand conjugates which naturally provides proper surface orientation, thereby improving bioassay performance. For example, as described above, the G5 dendrimer should typically have about 75% hydroxyl and 25% primary amine surface functional groups. In contrast, the G6 to G10 dendrimers should have greater than about 75% hydroxyl groups and less than about 25% primary amine groups in order to optimize surface orientation and reduce non-specific bindings. In addition, for G1 and G2 dendrimers, the surface functional groups should comprise less than about 20% hydroxyl groups and more than about 80% primary amine groups in order to optimize surface orientation. Finally, for G3 and G4 dendrimers, the surface functional groups should comprise less than about 50% hydroxyl groups and greater than about 50% primary amine groups to optimize surface orientation.

The nano-orientation concept of the present invention was further demonstrated by two separate experiments. The first experiment included modifications of colloidal gold particle surface with either a Fab antibody (for botulinum (bot) toxin) or a dendrimer-Fab antibody (antibot) conjugate, thus generating antibody coated colloidal gold conjugates. Since the bot Fab antibody in the former case has no orientation preference when adsorbed onto the colloidal gold surface, a crosslinked colloidal gold cluster was immediately formed upon addition of antibodies (because both head and tail portions of the bot Fab antibody were adsorbed onto the gold particle surface) as is shown in FIG. 7. After addition of bot toxoid, only a marginal increase in cluster sizes was observed because the presence of pre-crosslinked gold particles resulted in very little contrast. In another control experiment, upon the addition of primary amine ($NH_2$) modified dendrimer to colloidal gold, a crosslinked colloidal gold cluster was immediately formed. This indicated that 100% primary amine modified dendrimer has a very strong adhesion towards the colloidal gold surface.

In contrast, with a primary amine ($NH_2$) modified dendrimer-bot Fab conjugate, much smaller clusters were generated. Since neither dendrimer nor Fab component gave such a result, the formation of smaller aggregates suggested that a preferential orientation of this conjugate (i.e. dendrimers preferentially adsorbed on the gold surface due to strong charge attractions) occurred during reaction of colloidal gold with primary amine modified dendrimer-Fab conjugates. However, due to the large amount of primary amine groups on the dendrimer portions of the conjugates, there is still a significant amount of non-specific bindings between the dendrimer and different colloidal gold particles, resulting in lightly cross-linked products, i.e., false positives. However, these false positive reactions can be dramatically improved by using a mixed OH/NH2 dendrimer-bot Fab conjugate. Upon the addition of such conjugates, only individually dispersed gold particles were observed indicating that the mixed surface dendrimer-Fab conjugates were fully oriented on each colloidal gold particle surface such that no crosslinked clusters could be generated. In other words, no gold particles were connected with each other through the interactions of excess primary amine surface functional groups on the mixed surface dendrimer portion of the conjugates. The dispersed mixed surface dendrimer-Fab coated gold particles are shown in FIG. 8. In order to verify that the mixed surface dendrimer portion was in direct contact with the gold surface and the Fab portion was indeed on top of the mixed surface dendrimers, a small amount of bot toxoid (i.e. 100 ng/ml) was added to the dendrimer-Fab coated colloidal gold solution. As a result, giant colloidal gold particle clusters were immediately formed upon the addition of bot toxoid (i.e. at 100 ng/ml, FIG. 9). This result suggested that after being coated on the colloidal gold surface, the Fab portion was still capable of binding bot toxoid without any steric hindrance. Therefore, it indicated that the Fab molecules were indeed self-oriented toward the surface of the nanofilm coated on each gold particle. As a result, antibody functionalized, individually dispersed colloidal gold particles are formed, which can further react with antigens to generate giant clusters. Since no gold clusters were produced before the addition of antigens, the mixed surface dendrimer-antibody conjugate based immunogold assays generally exhibit much higher sensitivity and no false positive reactions. This is in sharp contrast with the antibody-based immunogold assays where low sensitivity and false positive readings have been consistently observed.

In addition, a lateral flow immunoassay ticket format was also utilized to demonstrate this nano-orientation effect. The current ticket is constructed by depositing the same antibody on both a membrane and a colloidal gold surface, respectively (as both capture and detector antibodies). As is shown in FIG. 2, when an antibody is applied on a membrane or a gold particle surface it can establish different orientations, of which only the "heads-up" orientation contributes to the antigen binding events. This assay configuration exhibits very low sensitivity and many false positive problems.

The lateral flow immunoassays constructed here included four different combinations as listed in Table 1. In addition to assay #1 (a control assay, which utilized the Fab antibodies for both capture and detector purposes), three additional assays based on mixed surface dendrimer-Fab conjugates were developed. When a mixed surface dendrimer-antibody conjugate was deposited on a surface (i.e. ticket membrane surface), all of the antibodies will be nanoscopically oriented as shown in FIG. 11. As a result, a much higher antigen binding efficiency was obtained. The assay sensitivity was found to be further improved by using mixed surface dendrimer-Fab conjugate coated colloidal gold particles. In this case, up to 100-fold sensitivity enhancement was achieved when compared with the pure antibody based assays. The detection limit for botulinum toxoid using this mixed surface dendrimer-antibody assay configuration can easily reach the 1 ng/ml level, while for the prior art antibody based assays constructed under the same conditions it is only about 100 ng/ml, see Table 2. More importantly, the dendrimer-based ticket assays do not have any false positive reactions.

TABLE 1

| Assay # | Capture ligand | Detector ligand | Reporter Gold Particle Diameter |
|---|---|---|---|
| 1 | Fab | Fab | 55 nm |
| 2 | Dendrimer-Fab | Fab | 55 nm |
| 3 | Fab | Dendrimer-Fab | 55 nm |
| 4 | Dendrimer-Fab | Dendrimer-Fab | 55 nm |

TABLE 2

| Detection Limit (ng/ml) | 250 | 125 | 25 | 5 | 1 | Interferents |
|---|---|---|---|---|---|---|
| Dendrimer-Ticket | + | + | + | + | + | − |
| Detection Time (min.) | <1 | 3 | 7 | 10 | 15 | |
| Ab-Ticket | + | + | − | − | − | + |
| Detection Time (min.) | 5 | 10 | | | | |

In this case, the dendrimer-ticket row from Table 2 corresponds to assay 4 from Table 1, while the Ab-ticket row corresponds to assay 1.

EXAMPLES

Materials: Different sizes of Polyamidoamine (PAMAM) and Polypropylene amine (PA) dendrimers were purchased from Dendritech, MI., and DSM (Netherlands), while PEI dendrigrafts and colloidal gold particles were prepared according to procedures published in the literature (Yin, R. et. al. *PMSE* 1995, 73, 277; and G. Frens, et. al, Nature Physical Science, Vol 241, Jan. 1, 1973, 20). All of the antibodies including Fab of anti-Botulinum toxin were provided by U.S Army Edgewood Chemical Biological Center (ECBC), Aberdeen Proving Ground, MD. The MAL-PEG-NHS (MW 2000) was purchased from Shearwater Polymer, Inc. Huntsville, Ala. The sulfosuccinimidyl 6-[3-(2-pyridyldithio)-propionamido]hexanoate(sulfo-LC-SPDP) and the 5,5'-dithiobi(2-nitrobenzoic acid) (DTNB) were purchased from Pierce, Rockford, Ill.

The preparation of dendrigraft-IgG conjugate is provided as a general procedure for the preparation of full antibody-dendritic polymer conjugates. Other conjugates such as E1-IgG, E2-IgG, E3-IgG, E4-IgG, E5-IgG, E6-IgG, E7-IgG, E8-IgG, E9-IgG, E10-IgG PA32-IgG, PA64-IgG, E1 (OH/NH$_2$ mix)-IgG, E2 (OH/NH$_2$ mix)-IgG, E3 (OH/NH$_2$ mix)-IgG, E4 (OH/NH$_2$ mix)-IgG, E5 (OH/NH$_2$ mix)-IgG, E6 (OH/NH$_2$ mix)-IgG, E7 (OH/NH$_2$ mix)-IgG, E8 (OH/NH$_2$ mix)-IgG, E9 (OH/NH$_2$ mix)-IgG, E10 (OH/NH$_2$ mix)-IgG were synthesized in a similar manner. Of course, E-series dendritic polymers are commercially available and are well known to those of ordinary skill in the art. PA-series are also well known and are commercially available from DSM (Netherlands). The mixed surface PAMAM and PA dendrimers were prepared according to procedures published by D. A. Tomalia, et al. (*Polym. J. (Tokyo)* 17, 117–132 (1985)), except that a mixture of ethylenediamine and monoethanolamine was utilized during the amidation step.

Preparation of IgG-Dendritic Polymer Conjugates

Iodoacetyl Dendrigraft: To a test tube containing 1 ml of 10–50 mg/ml of primary amine terminated dendrigraft (MW=30,000) in water is added 0.2 ml of 0.5 M sodium phosphate (pH 7.0), and the solution pH was then adjusted up to 7.6 using 1 N HCl. This solution was then added to freshly dissolved sulfo-SIAB (20 mg/ml in water), and vortexed gently. After incubation at 30° C. for one hour (or at room temperature for 2 hours), the pure product was obtained by passing the reaction mixture through a G-25 Sephadex column. The concentration of the polymer was determined using a fluorescamine assay monitored with a fluorimeter and the iodo content was quantified with DTT and 4,4'-dithiodipyridine.

Preparation of protein with SH groups: The anti-CKMB IgG protein is buffer exchanged into a reduction buffer (0.1 M sodium phosphate, 5 mM EDTA, (pH 6) and the resulting concentration was adjusted to 5 mg/ml. To this solution was added a solution of 11.4 mg/ml of DTT equal to ⅛ of the volume of the protein solution. After incubation at 37° C. for one hour, the free sulfhydryl groups were formed and the product was purified from low molecular reagents by a passage through a G-25 Sephadex column. The protein concentration was determined by UV at 280 nm.

Antibody-Dendrigraft Conjugate: To a test tube was added iodoacetyl modified dendrigraft and IgG-SH at challenge ratio of 3:1 (pH=7.6, protein conc.=5 mg/ml). After incubation at 2–8° C. for 16–24 hours, the reaction was quenched by addition of 20 mg/ml N-ethyl maleimide in DMF at 2–8% for 2 hours. The pure conjugate was obtained by gel filtration (Ultrogel AcA, Pharmacia Sephadex or Sepharose gels) or by ultrafiltration with YM-100 Amicon Membrane.

Preparation of Fab-Dendritic Polymer Conjugates

The preparation of E5-Fab conjugate is provided as a general procedure for the preparation of Fab-dendritic polymer conjugates. Other conjugates such as E1-Fab, E2-Fab, E3-Fab, E4-Fab, E5-Fab, E6-Fab, E7-Fab, E8-Fab, E9-Fab, E10-Fab, PA32-Fab, PA64-Fab, E1 (OH/NH$_2$ mix)-Fab, E2 (OH/NH$_2$ mix)-Fab, E3 (OH/NH$_2$ mix)-Fab, E4 (OH/NH$_2$ mix)-Fab, E5 (OH/NH$_2$ mix)-Fab, E6 (OH/NH$_2$ mix)-Fab, E7 (OH/NH$_2$ mix)-Fab, E8 (OH/NH$_2$ mix)-Fab, E9 (OH/NH$_2$ mix)-Fab, E10 (OH/NH$_2$ mix)-Fab were synthesized in a similar manner.

LC-SPDP PAMAM Dendrimer (E5): To the dendrimer ($500 \times 10^{-9}$ mol) in 500 µl of phosphate buffer (20 mM phosphate and 0.1 M NaCl, pH 7.5) was added $5.0 \times 10^{-6}$ mol of sulfo-LC-SPDP (1) in 100 µl of water. This was vortexed for one minute and incubated at 30° C. for 30 minutes. The LC-SPDP-E5 was purified by gel filtration chromatography on a PD-10 column and equilibrated with buffer A (0.1 M phosphate, 0.1 M NaCl and 5 mM EDTA, pH 6.8). The LC-SPDP-E5 was further washed and concentrated with phosphate buffer A to yield 420 µl of the concentrated solution.

Thiolated Dendrimer from LC-SPDP PAMAM Dendrimer (E5): The LC-SPDP dendrimer (80.3 nmol in 100 µl of buffer A) was mixed with 100 µl of dithiothreitol (DTT) (50 mM in buffer A) and was allowed to incubate at 20° C. for 15 minutes. DTT and the by-products were removed by continuously washing with buffer A and concentrating to yield 310 µl of the thiolated dendrimer which was used for conjugation with the activated Fab of anti-botulinum toxin B.

Maleimide PEG activated Fab of Anti-Botulinum Toxin B: The Fab (5 ml, 675 µg/ml) was concentrated and exchanged into PBS to leave 230 µl. To 80 µl of the concentrated Fab solution (ca. 27 nmol) was added 10.8 µl of al MAL-PEG-NHS solution (10 mM in water). This mixture was vortexed and incubated at 30° C. for 15 minutes. It was purified on a PD-10 column with buffer A. The maleimide-PEG activated Fab in 2.1 ml was used for conjugation with the reduced LC-SPDP dendrimer.

PAMAM Dendrimer (E5)-Fab of Anti-Botulinum toxin B Conjugate: To 310 µl (72 nmol) of the reduced LC-SPDP-PAMAM dendrimer (E5) was added the maleimide-PEG-Fab (2.1 ml, 2.4 nmol). The reaction mixture was concentrated to approximately 150 µl, which was allowed to incubate overnight at 4° C. Upon completion, the reaction was quenched, and the conjugate was then fractionated on a carboxymethyl cellulose column (3.5 ml) with a sodium chloride step gradient in 20 mM phosphate buffer at pH 7.4. The conjugate was characterized by the cationic exchange chromatography, UV spectroscopy with $\lambda_{max}$=278 nm, polyacrylamide gel electrophoresis and immunoreactivity by ELISA.

Colloidal Gold Based Immunoassays

Preparation of Gold-Ab Conjugates

A 125 ml flask was charged with 60 ml of colloidal gold solution (20–80 nm in diameter, O.D. 1.078). The pH of the solution was adjusted to 8–11 by addition of a 0.2 M potassium carbonate solution. A teflon-coated magnetic stirbar was added to the solution, and while stirring, 600 µl of conjugated antibody solution (O.D. 0.1–1.5 in sodium borate buffer) was added. The solution was stirred for 1 minute, followed by subsequent addition of 600 µl of bovine serum albumin (20% with sodium azide stabilizer). The mixture was stirred at 20° C. for 20–60 more minutes. The solution remained purple in color and some foaminess was observed. Upon completion, the stirbar was removed, and reaction mixture was transferred to two 50 ml conical tubes. The material was centrifuged until very little color was observed in the supernatant. The supernatant was removed and 400 µl of 25 mM sodium borate buffer was added in each tube. The contents were mixed thoroughly and the two tubes of material were combined and characterized by UV-Vis.

Lateral Flow Immunoassay Ticket Experiment

To compare the sensitivity of dendrimer-Ab and Ab based lateral flow immunoassays, four different assay configurations were constructed, see Table 1. In these assays, capture Ab was sprayed onto a cellulose membrane surface, while the Ab-Dendrimer-gold (detector) conjugate was placed on a conjugate release pad, and was placed underneath the adsorbent pad. The control line was sprayed with anti-mouse (Fab) antibody. The ticket strip is placed into a plastic housing. The total weight of this ticket is about 4.5 g, and the dimension is 2 cm (width)×7 cm (length)×0.5 cm (thickness). A series of samples with toxoid concentrations ranging from 1–250 ng/ml (in a total volume of 100 µl) were prepared for the test. Once the sample solution is added dropwise over 5 seconds to the adsorbent pad (the time is noted), the solution will flow laterally based on the capillary effect. The gold-Ab or gold-dendrimer-Ab conjugate will be released as soon as the solution passing through the conjugate release pad. If the test is positive, both control and test will turn red due to the formation of immunocomplexes, and the red color results from the colloidal gold particles. If the test is negative, only the control line will turn red and no color will appear on the test line due to the absence of "sandwich" immuno complexes at the test line/capture Ab sites. The time required for detection is 15 minutes, and the assay results are listed in Table 2.

Transmission Electron Microscopy Experiment

Figure 7:
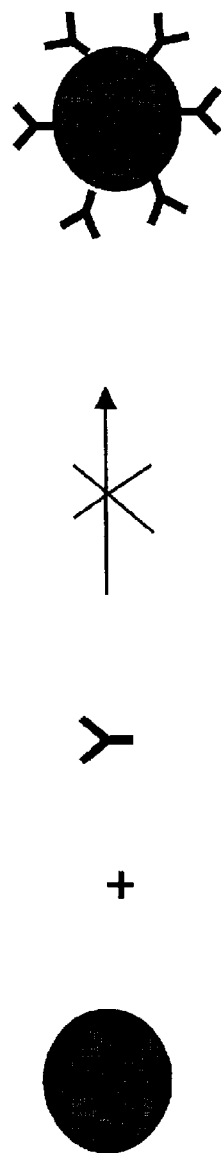
FIG. 7 is a schematic showing of the synthesis and characterization of colloidal gold-Fab conjugates without the use of dendrimers for orientation resulting in crosslinked colloidal gold particles.
Figure 7:
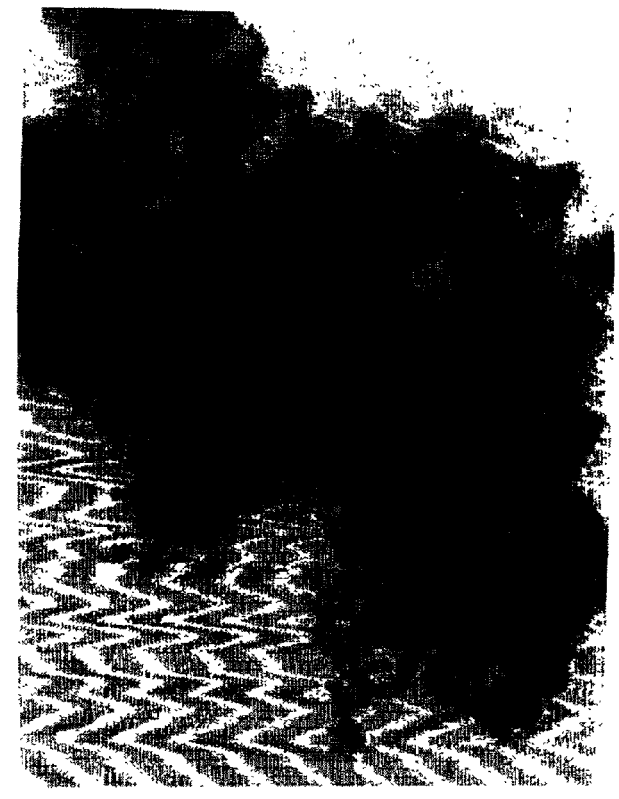
Figure 7:
Figure 8:
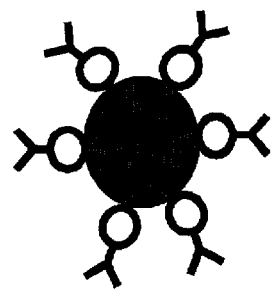
FIG. 8 is a schematic showing the synthesis and characterization of colloidal gold-dendrimer-Fab conjugates having improved self-orientation and without the formation of crosslinked colloidal gold particles.
Figure 8:
Figure 8:
Figure 8:
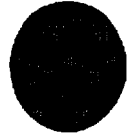
Figure 8:
Figure 8:
Figure 9:
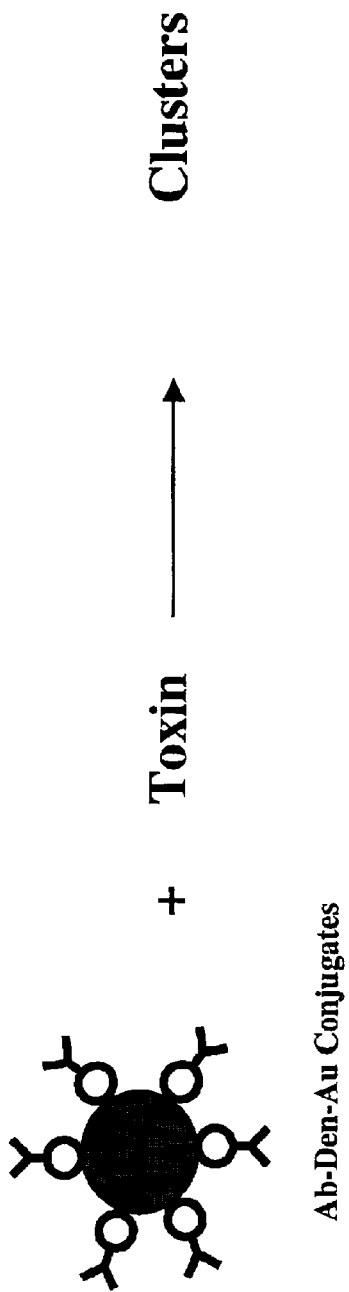
FIG. 9 is a schematic showing the result of the addition of Botulinum toxoid to a gold-dendrimer-Fab conjugate solution as characterized by TEM.
Figure 9:
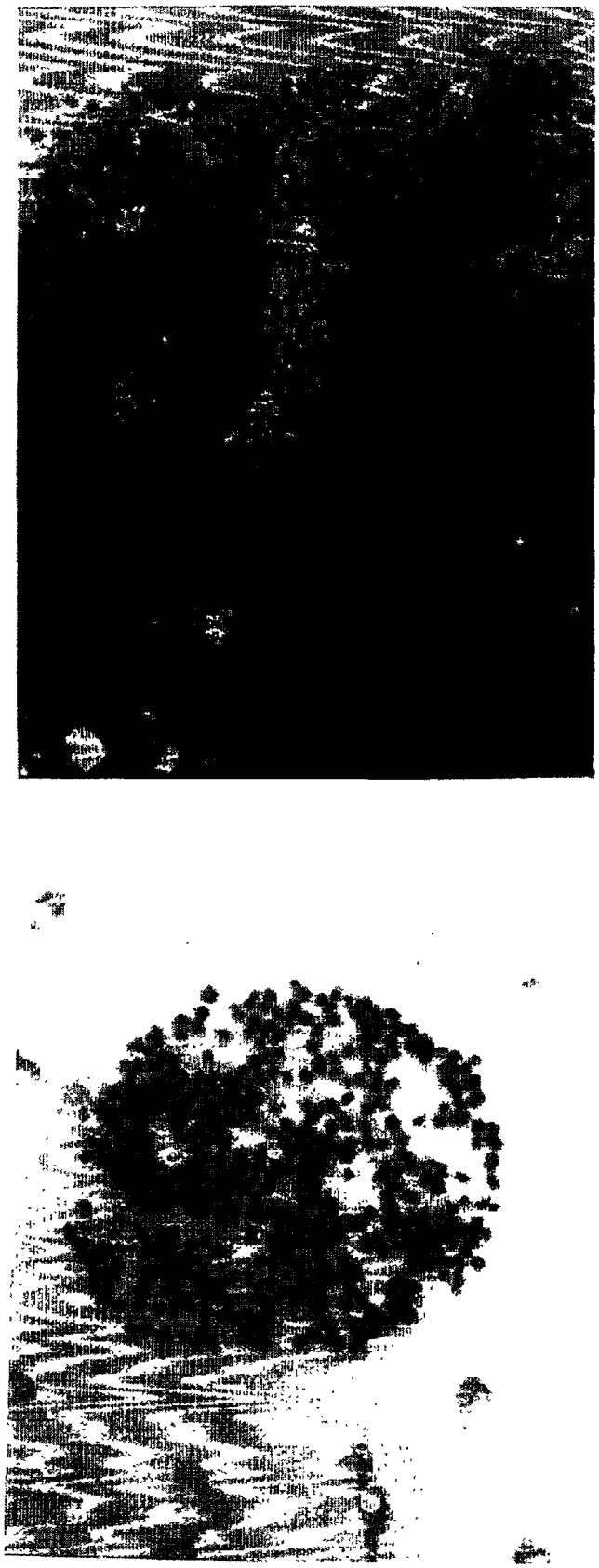
Figure 10:
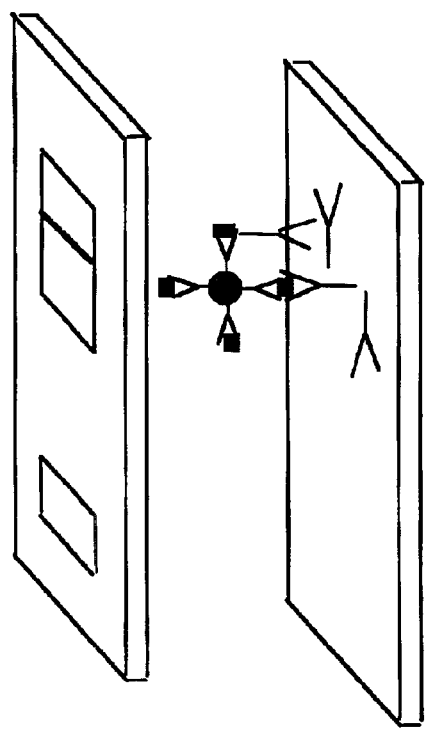
FIG. 10 is an illustration showing the capture and reporter antibodies of the current hand-held immunoassay tickets applied onto a surface through a random deposition method.
Figure 10:
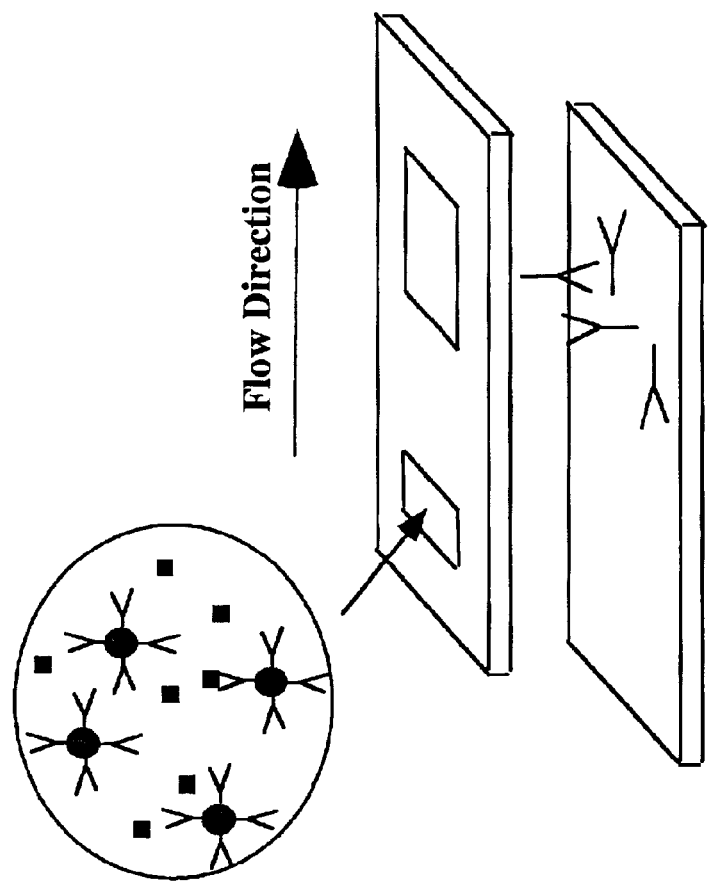

The Ab-gold and Ab-dendrimer-gold conjugate solutions were prepared, and divided into two portions. To one, toxoid was further added (final concentration is 100 ng/ml) while the other was used as a control. The TEM experiment was performed on a Phillips transmission electron microscope at magnifications of 530×, 4,400×, 11,500× and 40000×. The resulting image was enhanced by an Image Pro Image Processor and printed on a Sony video printer. A NIST traceable diffraction grating standard was used to calibrate the magnification values. The images generated by the TEM experiments are shown in FIGS. 7, 8, and 9.

It will be apparent to one skilled in the art that various changes, alterations, and modifications of the present invention are possible in light of the above teachings. It is therefore to be understood that while the invention has been described in this specification with some particularity, it is not intended to limit the invention to the particular embodiments provided herein. On the contrary, it is intended to cover all alternatives, modifications, and equivalents as may be included within the spirit and scope of the invention as defined in the appended claims.

What is claimed is:

1. A composition of matter, comprising:
   a molecularly compact polymer-ligand conjugate capable of self-orienting on a surface, wherein said molecularly compact polymer comprises a fifth-generation (G5) polyamidoamine dendrimer having surface functional groups, wherein said surface functional groups comprise about 75% hydroxyl groups and about 25% primary amine groups, and wherein said ligand is selected from the group consisting of T-helper cell CD4 molecule, Fc receptor, Acetylcholine receptor (AChR), T cell receptor for antigen, insulin receptor, hormone receptor, antibodies, antibody fragments, IgG molecules, Fab antibody molecules, polypeptides, DNA fragments, RNA fragments, hormones, insulin, hCG, enzymes, sialic acid, porphyrins, and nucleotides, and wherein said ligand is bound to said molecularly compact polymer and said molecularly compact polymer binds to said surface such that said ligand is substantially uniformly positioned opposite said surface.

2. The composition of matter of claim 1, wherein said ligand is selected from the group consisting of IgG molecules and Fab antibody molecules.

3. The composition of matter of claim 1, wherein said surface is selected from the group consisting of immunoassay test strips, glass, nitrocellulose, paper, quartz, plastics, colloidal particles, metals, polymer latex beads, clays, ceramics, up-converting phosphorescent particles, and quantum dots.

4. The composition of matter of claim 3, wherein said colloidal particles are selected from the group consisting of colloidal gold, colloidal silver, and colloidal platinum.

5. The composition of matter of claim 4, wherein said colloidal gold particles have a diameter in the range of from about 10 nm to about 80 nm.

6. The composition of matter of claim 5, wherein said colloidal gold particles have a diameter in the range of from about 45 nm to about 65 nm.

7. The composition of matter of claim 3, wherein said quantum dots are nanometer sized inorganic particles.

8. The composition of matter of claim 7, wherein said quantum dots are selected from the group consisting of cadmium sulfide, cadmium selenide, and zinc sulfide.

9. The composition of matter of claim 1, wherein said G5 polyamidoamine dendrimer is of about 5.4 nm in diameter.

10. The composition of matter of claim 1, wherein said molecularly compact polymer-ligand conjugate is used on a lateral flow immunoassay test strip, said test strip having a membrane surface, a conjugate release pad, and an absorbent pad.

11. The composition of matter of claim 10, wherein said molecularly compact polymer-ligand conjugate is bound to a colloidal gold particle and is used as a reporter ligand on said conjugate release pad.

12. The composition of matter of claim 10, wherein said molecularly compact polymer-ligand conjugate is used as a capture ligand on said membrane surface.

13. A composition of matter, comprising:
a molecularly compact polymer-ligand conjugate capable of self-orienting on a surface, wherein said molecularly compact polymer comprises a sixth-generation (G6) to tenth-generation (G10) polyamidoamine dendrimer having surface functional groups, wherein said surface functional groups comprise greater than or equal to 75% hydroxyl groups and less than or equal to 25% primary amine groups, and wherein said ligand is selected from the group consisting of T-helper cell CD4 molecule, Fc receptor, Acetylcholine receptor (AChR), T cell receptor for antigen, insulin receptor, hormone receptor, antibodies, antibody fragments, IgG molecules, Fab antibody molecules, polypeptides, DNA fragments, RNA fragments, hormones, insulin, hCG, enzymes, sialic acid, porphyrins, and nucleotides, and wherein said ligand is bound to said molecularly compact polymer and said molecularly compact polymer binds to said surface such that said ligand is substantially uniformly positioned opposite said surface.

14. The composition of matter of claim 13, wherein said ligand is selected from the group consisting of IgG and Fab antibody molecules.

15. The composition of matter of claim 13, wherein said surface is selected from the group consisting of immunoassay test strips, glass, nitrocellulose, paper, quartz, plastics, colloidal particles, metals, polymer latex beads, clays, ceramics, up-converting phosphorescent particles, and quantum dots.

16. The composition of matter of claim 15, wherein said colloidal particles are selected from the group consisting of colloidal gold, colloidal silver, and colloidal platinum.

17. The composition of matter of claim 16, wherein said colloidal gold particles have a diameter in the range of from about 10 nm to about 80 nm.

18. The composition of matter of claim 17, wherein said colloidal gold particles have a diameter in the range of from about 45 nm to about 65 nm.

19. The composition of matter of claim 15, wherein said quantum dots are nanometer sized inorganic particles.

20. The composition of matter of claim 19, wherein said quantum dots are selected from the group consisting of cadmium sulfide, cadmium selenide, and zinc sulfide.

21. The composition of matter of claim 13, wherein said G6 to G10 polyamidoamine dendrimers have diameters of about 6.7 nm to about 13.8 nm.

22. The composition of matter of claim 13, wherein said molecularly compact polymer-ligand conjugate is used on a lateral flow immunoassay test strip, said test strip having a membrane surface, a conjugate release pad, and an absorbent pad.

23. The composition of matter of claim 22, wherein said molecularly compact polymer-ligand conjugate is bound to a colloidal gold particle and is used as a reporter ligand on said conjugate release pad.

24. The composition of matter of claim 22, wherein said molecularly compact polymer-ligand conjugate is used as a capture ligand on said membrane surface.

25. A composition of matter, comprising:
a molecularly compact polymer-ligand conjugate capable of self-orienting on a surface, wherein said molecularly compact polymer comprises a first-generation (G1) to second-generation (G2) polyamidoamine dendrimer having surface functional groups, wherein said surface functional groups comprise less than or equal to 20% hydroxyl groups and greater than or equal to 80% primary amine groups, and wherein said ligand is selected from the group consisting of T-helper cell CD4 molecule, Fc receptor. Acetylcholine receptor (AChR), T cell receptor for antigen, insulin receptor, hormone receptor, antibodies, antibody fragments, IgG molecules, Fab antibody molecules, polypeptides, DNA fragments, RNA fragments, hormones, insulin, hCG, enzymes, sialic acid, porphyrins, and nucleotides, and wherein said ligand is bound to said molecularly compact polymer and said molecularly compact polymer binds to said surface such that said ligand is substantially uniformly positioned opposite said surface.

26. The composition of matter of claim 25, wherein said ligand is selected from the group consisting of Fab antibody molecules and polypeptide molecules.

27. The composition of matter of claim 25, wherein said surface is selected from the group consisting of immunoassay test strips, glass, nitrocellulose, paper, quartz, plastics, colloidal particles, metals, polymer latex beads, clays, ceramics, up-converting phosphorescent particles, and quantum dots.

28. The composition of matter of claim 27, wherein said colloidal particles are selected from the group consisting of colloidal gold, colloidal silver, and colloidal platinum.

29. The composition of matter of claim 28, wherein said colloidal gold particles have a diameter in the range of from about 10 nm to about 80 nm.

30. The composition of matter of claim 29, wherein said colloidal gold particles have a diameter in the range of from about 45 nm to about 65 nm.

31. The composition of matter of claim 27, wherein said quantum dots are nanometer sized inorganic particles.

32. The composition of matter of claim 31, wherein said quantum dots are selected from the group consisting of cadmium sulfide, cadmium selenide, and zinc sulfide.

33. The composition of matter of claim 25, wherein said G1 to G2 polyamidoamine dendrimers have a diameter of about 2.2 nm to about 2.9 nm.

34. The composition of matter of claim 25, wherein said molecularly compact polymer-ligand conjugate is used on a lateral flow immunoassay test strip, said test strip having a membrane surface, a conjugate release pad, and an absorbent pad.

35. The composition of matter of claim 34, wherein said molecularly compact polymer-ligand conjugate is bound to a colloidal gold particle and is used as a reporter ligand on said conjugate release pad.

36. The composition of matter of claim 34, wherein said molecularly compact polymer-ligand conjugate is used as a capture ligand on said membrane surface.

37. A composition of matter, comprising:
a molecularly compact polymer-ligand conjugate capable of self-orienting on a surface, wherein said molecularly compact polymer comprises a third-generation (G3) to fourth-generation (G4) polyamidoamine dendrimer having surface functional groups, wherein said surface functional groups comprise less than or equal to 50% hydroxyl groups and greater than or equal to 50% primary amine groups, and wherein said ligand is selected from the group consisting of T-helper cell CD4 molecule, Fc receptor, Acetylcholine receptor (AChR), T cell receptor for antigen, insulin receptor, hormone receptor, antibodies, antibody fragments, IgG molecules, Fab antibody molecules, polypeptides, DNA fragments, RNA fragments, hormones, insulin, hCG, enzymes, sialic acid, porphyrins, and nucleotides, and wherein said ligand is bound to said molecularly compact polymer and said molecularly compact polymer binds to said surface such that said ligand is substantially uniformly positioned opposite said surface.

38. The composition of matter of claim 37, wherein said ligand is selected from the group consisting of IgG molecules and Fab antibody molecules.

39. The composition of matter of claim 37, wherein said surface is selected from the group consisting of immunoassay test strips, glass, nitrocellulose, paper, quartz, plastics, colloidal particles, metals, polymer latex beads, clays, ceramics, up-converting phosphorescent particles, and quantum dots.

40. The composition of matter of claim 39, wherein said colloidal particles are selected from the group consisting of colloidal gold, colloidal silver, and colloidal platinum.

41. The composition of matter of claim 40, wherein said colloidal gold particles have a diameter in the range of from about 10 nm to about 80 nm.

42. The composition of matter of claim 41, wherein said colloidal gold particles have a diameter in the range of from about 45 nm to about 65 nm.

43. The composition of matter of claim 39, wherein said quantum dots are nanometer sized inorganic particles.

44. The composition of matter of claim 43, wherein said quantum dots are selected from the group consisting of cadmium sulfide, cadmium selenide, and zinc sulfide.

45. The composition of matter of claim 37, wherein said G3 to G4 polyamidoamine dendrimers have a diameter of about 3.6 nm to about 4.5 nm.

46. The composition of matter of claim 37, wherein said molecularly compact polymer-receptor conjugate is used on a lateral flow immunoassay test strip, said test strip having a membrane surface, a conjugate release pad, and an absorbent pad.

47. The composition of matter of claim 46, wherein said molecularly compact polymer-ligand conjugate is bound to a colloidal gold particle and is used as a reporter ligand on said conjugate release pad.

48. The composition of matter of claim 46, wherein said molecularly compact polymer-ligand conjugate is used as a capture ligand on said membrane surface.

49. A composition of matter, comprising:
a molecularly compact polymer-ligand conjugate capable of self-orienting on a surface, wherein said molecularly compact polymer comprises a fifth-generation (G5) polyamidoamine dendrimer having surface functional groups, wherein said surface functional groups comprise about 75% hydroxyl groups and about 25% primary amine groups, and wherein said ligand is selected from the group consisting of antibodies, antibody fragments, Fab antibody molecules, polypeptides, DNA fragments, RNA fragments, enzymes, sialic acid, porphyrins, nucleotides, and IgG molecules, and wherein said ligand is bound to said molecularly compact polymer and said molecularly compact polymer binds to said surface such that said ligand is substantially uniformly positioned opposite said surface, and wherein said surface comprises colloidal gold particles.

50. The composition of matter of claim 49, wherein said molecularly compact polymer-receptor conjugate is used on a lateral flow immunoassay test strip.

* * * * *